United States Patent
Seaver

(10) Patent No.: US 9,371,243 B1
(45) Date of Patent: *Jun. 21, 2016

(54) MICROCHLORINE GENERATION FOR ANTI-BIOFOULING

(71) Applicant: SeaLite Engineering, Inc., Cataumet, MA (US)

(72) Inventor: George A. Seaver, Cataumet, MA (US)

(73) Assignee: SeaLite Engineering, Inc., Cataumet, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/726,948

(22) Filed: Jun. 1, 2015

Related U.S. Application Data

(63) Continuation of application No. 13/031,180, filed on Feb. 18, 2011, now Pat. No. 9,090,492.

(51) Int. Cl.
| | | |
|---|---|---|
| *C02F 1/46* | (2006.01) | |
| *A01N 59/00* | (2006.01) | |
| *C02F 1/467* | (2006.01) | |
| *C02F 103/08* | (2006.01) | |

(52) U.S. Cl.
CPC ........... *C02F 1/4674* (2013.01); *C02F 2103/08* (2013.01); *C02F 2201/46105* (2013.01); *C02F 2303/04* (2013.01)

(58) Field of Classification Search
CPC ......... A01N 59/00; A61L 2/18; C02F 1/4674; C02F 2209/40; C02F 2201/4611; C02F 2209/29
USPC ......... 210/739, 243, 746, 748.18, 87; 216/67; 427/569; 422/186.04, 22, 29; 73/861.18; 205/701

See application file for complete search history.

(56) References Cited

U.S. PATENT DOCUMENTS

| | | | |
|---|---|---|---|
| 4,097,356 A | 6/1978 | Yates | |
| 5,893,977 A | 4/1999 | Pucci | |
| 6,536,272 B1 | 3/2003 | Houston et al. | |
| 9,090,492 B2 | 7/2015 | Seaver | |
| 2002/0014460 A1* | 2/2002 | McKay | ........ C02F 1/4606 210/696 |
| 2007/0017820 A1 | 1/2007 | Anderson et al. | |
| 2011/0000797 A1 | 1/2011 | Henry | |
| 2011/0006039 A1 | 1/2011 | Swallow et al. | |

OTHER PUBLICATIONS

AquaCal Autopilot Manual: Pool Pilot Cubby Digital Salt Chlorine Generator, Feb. 14, 2008.

(Continued)

*Primary Examiner* — Walter D Griffin
*Assistant Examiner* — Cameron J Allen
(74) *Attorney, Agent, or Firm* — Patent Law Offices of Michael E. Woods; Michael E. Woods

(57) ABSTRACT

A method and an apparatus for retrofit hydrolization of seawater for production of halogen biocides in situ. A method for effecting an in situ generation of biocide as an aid in anti-biofouling of a device disposed in a volume of salt water includes a) associating a cathode electrode to the device; b) associating an anode electrode to the device with the anode electrode spaced apart from the cathode electrode; and c) hydrolyzing one or more components in the volume of salt water to generate a halogen biocide at the anode electrode with the biocide flowing from the anode electrode away from the cathode electrode as a biocide film, the film responsive to a physical arrangement of the associations of the electrodes with the device.

3 Claims, 4 Drawing Sheets

(56) References Cited

OTHER PUBLICATIONS http://www.seakeepers.org/technology.php, The Seakeekper 1000, Aug. 2008.

Smallwood, C., 1994: Drinking water criteria documents for chloramines. EPA Document # ECAO-CIN-D002 at www.epa.gov/ncea/pdfs/water/chloramine/dwchloramine.pdf.

Electrolyis of Water, Wikipedia.Org (http://en.wikipedia.org/wiki/Electrolysis_of_water), Mar. 15, 2011.

Hypochlorous Acid, Wikipedia.Org (http://en.wikipedia.org/wiki/Hypochlorous_acid), Mar. 15, 2011.

Chemetrics: Chlorine, http://www.chemetrics.com/chlorine, 2010.

Chemetrics, Inc.: Bromine (http://www.chemetrics.com/bromine) 2010.

Anthoni, Dr. J. Floor, 2010: The Chemical Composition of Seawater. www.seafriends.org.nz/oceano/seawater.htm.

Biocides, LENNTECH Water Treatment Solutions (http://www.lenntech.com/biocides.htm), Mar. 15, 2011.

* cited by examiner

MICROCHLORINE GENERATION FOR ANTI-BIOFOULING

CROSS REFERENCE TO RELATED APPLICATIONS

This Application is a Continuation of application Ser. No. 13/031,180 filed on Feb. 18, 2011, now U.S. Pat. No. 9,090,492, the contents of which are hereby expressly incorporated in its entirety by reference thereto for all purposes.

FIELD OF THE INVENTION

The present invention relates generally to oceanic anti-biofouling and more particularly, but not exclusively, to retrofit hydrolization of seawater for production of halogen biocides in situ.

BACKGROUND OF THE INVENTION

For over 30 years chlorine generation has been used by the swimming pool industry to keep pool water free of algae. A patent (U.S. Pat. No. 4,097,356) for such use was granted in 1978 with many granted since on chlorine generation. The use of generation over chlorine tablets is preferred in pools used year round, in salt water swimming pools and in marine animal rescue pods. A representative system for swimming pools provides a platinum-electroded cell in a recirculating system of the pool. Hydrolization of the recirculating pool water is turned on for a variable percentage of the time that recirculation occurs, the variation depending upon a number of factors including the temperature of the water, its pH and the bacterial load that the pool is under. For example, for a 10,000-gallon pool, the pump may recirculate pool water for eight hours a day with the hydrolization active for four hours, and consume about 36 watts. Fresh water pools require the addition of three parts per thousand (ppt) NaCl to operate; seawater pools generally require the same cycle time and chlorine levels as fresh water pools.

There are many organizations that use marine animal rescue pods for the recovery of injured marine animals to bring them back to their facilities. Some of these are located in tropical locations, e.g., on the Gulf of Mexico, which places a considerable bacteria and algae load on marine systems. There exist 36-watt chlorine generation systems that are able to manage the growth of marine organisms in various pod capacities, for example, 15,000 go 30,000-gallon pods.

Most manufacturers of oceanographic conductivity-temperature and depth (CTD) instruments employ some form of anti-biofouling device or technique. Some manufacturers are known to use copper mesh at an inlet to the sensors. Others use an anti-biofouling kit which is installed near the sensors of equipment probes for protection against biofouling. Still others use a chlorine generator pumped and cycled by their computer-controlled sampling system, which can provide 3-months protection on a Gulf of Mexico 3 meter buoy. Another solution sometimes used is provision of an anti-fouling toxic coating, Tributyltin (TBTO), within their conductivity sensors to ward off biofouling. It is common to be able to collect good data for 3-6 months before maintenance is necessary, although sediment can be a problem earlier.

The existing systems are generally capable of combating biofouling, when the system is designed with an in situ integral component. However, for systems which do not have a built-in anti-biofouling component, typical solutions include containment of the sensor within an enclosure.

Further, many existing systems generate, by some measure, too much biocide that can cause concern for disturbing the habitat in which the system operates. The systems essentially "flood" an area around the sensor with biocide to implement the anti-biofouling function. The biocide, not being targeted, must be generated in greater quantity. The generation of more quantity of non-targeted biocide, when the biocide is generated from an onboard power source, means that the power source is exhausted more quickly than would be the case if a more targeted, less quantity, biocide were produced.

What is needed is a retrofit hydrolization of seawater for production of directed and targeted halogen biocides in situ.

BRIEF SUMMARY OF THE INVENTION

The following summary of the invention is provided to facilitate an understanding of some of technical features related to retrofit, targeted hydrolization of salt water, including seawater for production of halogen biocides in situ, and is not intended to be a full description of the present invention. A full appreciation of the various aspects of the invention can be gained by taking the entire specification, claims, drawings, and abstract as a whole. Disclosed is a method and an apparatus for retrofit hydrolization of seawater for production of targeted halogen biocides in situ.

A method for effecting an in situ generation of biocide as a targeted aid in anti-biofouling of a device disposed in a volume of salt water includes a) associating a cathode electrode to the device; b) associating an anode electrode to the device with the anode electrode spaced apart from the cathode electrode; and c) hydrolyzing one or more components in the volume of salt water to generate a halogen biocide at the anode electrode with the biocide flowing from the anode electrode away from the cathode electrode as a biocide film, the film responsive to a physical arrangement of the associations of the electrodes with the device.

An apparatus for attaching to a device disposed in a volume of salt water includes a controller; two or more electrodes; a power source coupled to the two or more electrodes; and a foundation supporting the controller, the two or more electrodes, and the power source, the foundation retrofittable to the device to communicate the two or more electrodes to the volume of salt water proximate to the device; wherein the controller selectably applies an electric potential to the two or more electrodes from the power source to generate a directed halogen biocide film from a particular one electrode of the two or more electrodes with the generated halogen biocide film disposed toward the device by a boundary layer between the device and the volume of salt water.

An apparatus includes a cathode electrode located at a surface of a device including a first sensor with the device disposed in a volume of salt water; an anode electrode located at the surface, wherein a voltage applied across the electrodes produces a biocide film from the volume of salt water at the anode and wherein the biocide film has a relative motion to the first sensor with the biocide film flowing away from the anode and cathode and towards the first sensor; with the film disposed towards the surface by a boundary layer created responsive to the relative motion, wherein the biocide film flows over the first sensor within the boundary layer.

An apparatus including a first cathode electrode located at a first surface of a device with the device disposed in a volume of salt water; a first anode electrode located at the first surface, wherein a first voltage applied across the first electrodes produces a first biocide film from the volume of salt water at the anode and wherein the first biocide film has a first relative motion to the first surface with the first biocide film flowing away from the anode; with the first biocide film disposed towards the first surface by a first boundary layer created responsive to the first relative motion, wherein the first biocide film flows over the first surface within the first boundary layer.

Advantages of the present invention include lower quantities and concentrations of biocides that reduce negative environmental impacts; reduced power consumption to enable longer-term sensor operation without maintenance for power-source replacement and removing biofouling of the sensor. Another advantage of this method is that the halogen biocide eventually recombines with free sodium and other ions, leaving no toxic residue.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1(a), FIG. 1(b), and FIG. 2(c), illustrates one embodiment of an electrode configuration for producing directed halogen biocide by hydrolysis for use on ocean sensors, called a removable collar electrode;

FIG. 2(a), FIG. 2(b), and FIG. 2(c), illustrates a second embodiment of an electrode configuration for producing directed halogen biocide by hydrolysis, called a "stick-on film" electrode;

DETAILED DESCRIPTION OF THE INVENTION

Figure 1:
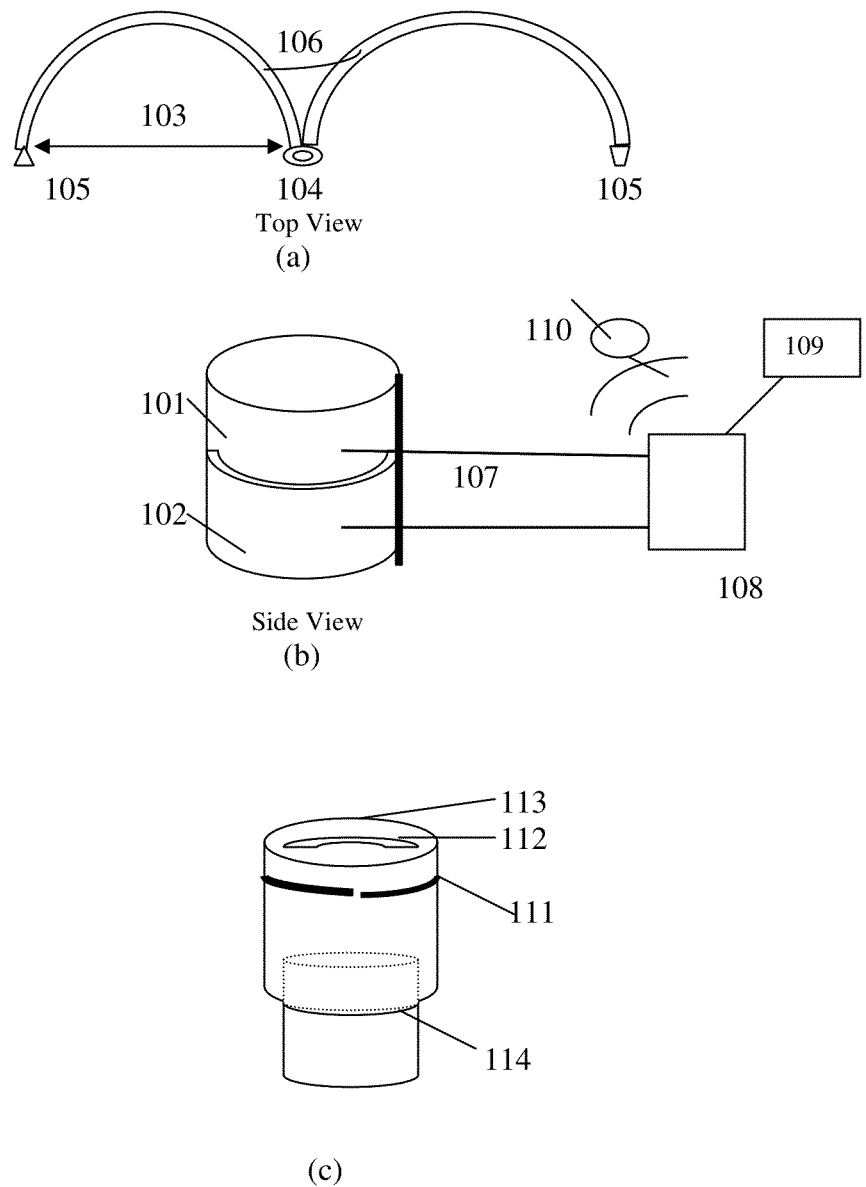
FIG. 1, including

Embodiments of the present invention provide a retrofit hydrolization of salt water, which includes seawater for production of directed halogen biocides in situ. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

SeaLite Engineering continues to perform research to understand the effect of free and combined chlorine and bromine on the several stages of biofouling in coastal waters. In preliminary work on the biofouling problem and using chlorine generation through hydrolysis, research was conducted to optimize its application and, thus, provide unattended sensor operation for at least one year in warm water environments at low power costs.

SeaLite Engineering has conducted laboratory experiments on the generation of chlorine in seawater. The goal was to determine the relationship between the power required, the distance between, size of and composition of the electrodes, and the movement of the hydrochlorous acid, hydrogen and oxygen bubbles created by the hydrolysis. Applying a voltage across a seawater gap produces:

at the cathode (negative pole):

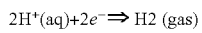

$$2H^+(aq) + 2e^- \Rightarrow H_2 \text{ (gas)}$$

In salt water, as chlorine is lower on the standard electrode potential than oxygen, chlorine gas is produced over oxygen gas at the anode (positive pole):

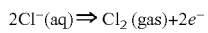

$$2Cl^-(aq) \Rightarrow Cl_2 \text{ (gas)} + 2e^-$$

If all of the current goes to producing $Cl_2$ over $O_2$ gas, and then all of the $Cl_2$ gas dissolves in the salt water, then the number of applied (potentially free) chlorine ions are:

(1) $Cl^- = I \times t \times 6.242 \times 10^{18}$, where I=amps, t=seconds and 1 amp=$6.242 \times 10^{18}$ electrons/sec.

However, the chlorine gas may not go entirely to free chlorine (as hydrochlorous acid, hypochlorite ion and dissolved $Cl_2$) which are the biocide agents:

(2) $nCl_2 \Rightarrow xHOCl \text{ (aq)} + yOCl + zCl_2$ (expelled gas), where $x+y/2+z=n$ and $z=F$(flow, electrode).

In pure salt water (NaCl), the function F is dependent upon the anode orientation, its shape and its material. In seawater an additional complication comes from its constituents of ammonia and organic nitrogen compounds that rapidly form what is termed 'combined' chorine (chloramines) and bromine that forms hypobromite. Although these are biocides, they are not detected with the free chlorine test.

The efficiency of the biocide process is dependent upon:
1. the excess potential over the cell reversible potential, dependent on electrode material, particularly at the anode $Cl^-$ electrode.
2. how much chlorine gas escapes the $OH^-$ ion attraction and leaves as $Cl_2$, dependent on the shape, orientation and electrode material.
3. The type and amount of combined chlorine that is also created SeaLite Engineering has found that some anode materials and shapes allow some $Cl_2$ to escape and other material limits that escape. The efficiency of converting electrical energy into chlorine chemical energy is estimated at 50%. Initial testing at SeaLite Engineering show that 40 to 140 mw for 1 minute is required to produce enough hydrochlorous acid to fully immerse a sensor package in 1-liter of seawater. The variation depends upon the shape (line, 1-D or sheet, 2-D) and the gap (15 to 25 mm) of the electrodes. The partitioning of chlorine gas between free and combined chlorine in seawater is an important parameter. Also, the type of metal used for the electrodes is important in order to minimize the voltage and power required and the electrode contamination to the seawater. The anode is particularly important, and platinum is the best choice, particularly for sustained use. Titanium is acceptable for the cathode, which experiences less erosion forces.

A preliminary experiment at about 7 ppm applied chlorine ion (~10 times greater than the minimum required) reduced the alga cell count from $1 \times 10^6$ cells/ml to nearly zero. There was no measurable free chlorine, and the biocidal effect began within 15 minutes of application. As seawater includes ammonia (0.003%) and Bromine (0.22%), chlorine combines with these constituents to become inorganic chloramines (called combined chlorine) and hypobromite. These are also biocides, weaker and longer lasting, are not detected as free chlorine and can be detected with iodide titration techniques. These preliminary results suggest that the concentration of free chlorine is dependent, not only upon the applied charge (of equation (1) above), but also upon time and the concentration of other constituents. The time for the re-growth of algae inside under a GroLite is about 20 days.

SeaLite Engineering, Inc. has conducted a quantitative study of the generation of free and combined chlorine from seawater, and then applied this knowledge to the protection of oceanographic sensor from algae growth. By reducing the power requirement to a minimum, long term unattended deployment of sensors and moorings will become possible using primarily recycled seawater chlorine. For a large generation of free chlorine the potential of pollution to the surrounding environment would be a concern. Preliminary tests show the desired antibiofouling effect occurs at sub-ppm chlorine levels with no measurable residual $Cl^-$. For cycling times of 1 minute/day, excess $Cl^-$ recombines with Na, as the 30-year experience of salt water swimming pools demonstrates. SeaLite Engineering's preliminary results for a static environment remained clear for 8 days, and then began to grow algae again.

Technological Benefits

Embodiments of the present invention improves upon the state of art of the anti-biofouling of ocean sensors and hulls by providing for:

1. remote activation of the chlorine biocide in in situ ocean operations when a biofilm just begins to appear.
2. the use of a proprietary empirical equation relating electric current to free chlorine concentration and then to algae biocide effect in order to apply the minimum $Cl^-$ amount required to inhibit algae growth at the sensor.
3. the introduction of free chlorine into the sensor body boundary layer created by the negatively buoyant $Cl^-$ biocide plume/film, thus greatly reducing the amount of $Cl^-$ needed over volumetric application.
4. the introduction of chlorine biocide into the boundary layer of a hull created by the forward motion of the vessel, thus causing the chlorine biocide to be confined to the boundary layer and to traverse the lateral length of the underwater part of the hull.
5. the use of sub-parts per million CF injection that leaves no residual free chlorine.
6. the application of chlorine biocide only when needed, for example, when an algae sensor, such as with a calibrated response test from the conductivity cell or detected fluorescence of the biofilm, indicate an algae film has just begun to appear. This incipient attack method forestalls future barnacle growth.
7. the application of gravity-driven Cr plume across a planar sensing surface, such as with a Critical Wavelength Refractometer.
8. the use of a computer microprocessor at the sensor or hull to accomplish (2), (3), (4), (5) and (6) above, for example, turning off the biocide cycle when the temperature drops below 10° C. or the depth becomes greater than 100 meters.
9. the use of a generic anti-biofouling kit for use on many different instruments.

Regarding (1) above for in situ ocean operations monitored in real time, innovation includes remote activation via satellite of a halogen (e.g., chlorine, bromine, or the like) biocide when the conductivity or other sensor readings indicated a compromised sensor. The biological load is quite variable, reflecting primarily the variability of temperature, sunlight and nutrients. A conductivity cell can be sensitive to early biofouling, particularly in its time response. Probing the cell with a calibrated step function signal will alert the on-board computer and/or the satellite command center of biofouling. Alternatively, illuminating the sensor with blue light would stimulate red fluorescence as a biofilm begins to develop; a detector focused on this sensor then signals the computer of this fact. In addition to conductivity, temperature and depth sensors, current meters deployed on floats and moorings will also be protected from large-scale macrophytes and barnacles jamming their operation by early intervention at the biofilm stage.

Both NOAA and NASA have ocean observational programs that specify deployment of salinity and other sensors in coastal areas for long periods of time. The Physical Oceanographic Real Time System (PORTS), the Integrated Ocean Observing System (IOOS) and the National Data Buoy Center (NDBC) of NOAA, and the Laboratory for Hydrospheric Processes of NASA/GSFC are four of these programs; the sensors used in these programs are frequently subject to biofouling.

NOAA, through the National Ocean Service (NOS) Center for Operational Oceanographic Products and Service (CO-OPS) runs the PORTS program. This program is presently operating in 18 of the largest harbors in the United States with from 1 to 50 instruments in each harbor. For example, in southern Chesapeake Bay there are 14 measurement stations reporting in real time, 4 of which report conductivity. These sensor systems now require monthly service calls and extending the service interval and reducing these costs is needed.

NOAA is also administrator of the IOOS programs which employ environmental sensors on buoys, gliders, and submerged structures for both emergency and management purposes, and biofouling is a major problem in carrying out that mission. The Director of NOAA IOOS specifically recommends chorine generation.

In addition, NASA is concerned with biofouling in many of its programs. In the ARGO float program, its CTD is turned off in the upper 5 meters of the float's profiling due to the threat of biofouling. Several attempts are being made to solve this near-surface salinity problem, due to the importance of it for satellite calibration. Chlorine generation would be suitable for this antibiofouling application. Also, NASA's GSFC/Wallops Island Laboratory for Hydrospheric and Biospheric Processes has developed autonomous surface vehicles (ASV) for air-sea interface observations in coastal and estuary environments, as well as for satellite calibration and validation, that require an antibiofouling capability.

The transocean thermal glider effort would benefit from this antibiofouling technology. Transatlantic tests of the Teledyne/WebbResearch RU27 glider found that by the Azores it had slowed considerably from biofouling on its body. Once this was removed it completed its journey. The U.S. Navy has authorized 154 of these sea gliders, and General Dynamics (Spray glider), Teledyne (RU27) and iRobot (Sea Glider) have begun the production of these vehicles. It has been found that these gliders require an antibiofouling capability to complete the transects that they were designed for.

Finally, the offshore oil drilling and production platforms are plagued by algae growth, particularly in the upper 100 meters of water, and need an antibiofouling capability.

Regarding (2) above the growth of bacteria, algae and larger marine organisms is largely dependent upon the temperature, sunlight and pH of the seawater. It is known that for summertime temperatures, sunlight and pH algae growth is dramatic. The level of chlorine required to inhibit this growth for swimming pools is 1 to 3 ppm free chlorine and for the control of bacterial growth in domestic water supplies it is 0.4 ppm chlorine, assuming pH values between 8 and 916 (estuary pH values range between 7.5 and 8 with occasional values out to 7 and 8.5).

To achieve this level of chlorine biocide for 1-liter of estuary water at 26° C. and about 25 ppt salinity, 1.2 volts across 1-D electrodes at a 25-mm gap produces a 10 ma current (12-mw power). From equation (1) above, under ideal conditions, a two minute, 0.01 amp current would produce $3.75 \times 10^{18}$ $Cl_2$ gas molecules as:

1 amp=$6.24 \times 10^{18}$ electrons/sec,

For 120 seconds this dissolves to become $7.5 \times 10^{18}$ HOCl molecules. Divided by Avogadro's Number, $6.02 \times 10^{23}$/mole, and times the molecular weight of Cl, this becomes about 0.4 ppm of chlorine, sufficient to inhibit bacterial-level growth. The next step is to determine how long it takes for that 0.4-ppm Cl to dissipate, and then how long before "slime" begins again the fouling process. That would set the required cycle time for the Cl generator.

The experimental response times for the effective chorine generation and cycling of equation (2) are:

a. biocide application ~1 min. e. algae regrowth (indoors, GroLite) ~8 days (film)
b. biocide algae kill ~15 min. """~21 days (full bloom)
c. conductivity recovery ~15 min. """(sun) ~5 days (begin)
d. measurement cycle ~>15 min. """~9 days (full bloom)

These results point out the measurement window between the algae suppression and conductivity recovery (15 minutes) and the algae re-growth (5 days). Understanding this minimizes the application of chlorine ions and the electrical energy required for that application.

In regards to (3) the detailed characteristics of the flow of hydrolyzed seawater for specific sensor configurations, some embodiments of the present invention exploit these characteristics to enhance the biocide effectiveness. In seawater, as chlorine is more favorably placed on the electrode potential series, chlorine gas will be produced in place of oxygen. As chlorine is soluble in water, some or all of this gas will combine with ammonium and Bromine or dissolve with water to form the biocide. The electrodes are configured so that the hydrogen bubbles rise quickly out of the way. As the chlorine ion compounds are three times heavier than water, they form a downward plume/film, either narrow pencil or thin sheet, depending upon the anode shape, and cling to the vertical or semi-vertical surface from which they were generated. (Substantially vertical refers to an angle sufficient to permit the descending biocide plume/film to cling appropriately.) Bubbles in the vicinity of the sensors, because of their lower conductivity and surface tension, effect the sensor output and are difficult to dislodge. The cathode has been designed to allow buoyancy to carry the $H_2$ bubbles clear of the instrument package.

The location and shape of the electrodes are preferably designed specifically for the traditional conductivity and temperature sensors that are in use by, for example, NOAA. First, the anode will be placed above the sensor to allow the hydrochlorous plume to move from gravity down over the sensor. Hydrochlorous acid is much heavier (3x) than salt water. For laminar or turbulent boundary layers, the layer remains on the generating surface, and the chlorine biocide will stay in the momentum boundary layer until severe curvatures cause the boundary layer to separate. This boundary layer can be caused by the negative buoyancy of the chlorine compound plume or by the forward movement of the sensor or vessel or other relative motion, such as the device disposed in a predictable current or the like. Applying the biocide into the boundary layer, as opposed to volumetrically, also addresses any environmental concerns regarding free chlorine. The slow flow conditions should insure that all the chlorine gas would be dissolved.

In regards to (4) the forward motion of a vessel in the ocean creates a boundary layer at the skin of the hull whereby the fluid exactly on the hull moves at the speed of the vessel, the fluid speed rapidly changing to that of the surrounding ocean in a short distance from the hull, this distance being determined by the viscosity of the fluid, the speed of the vessel and the distance from the beginning of the boundary layer. A halogen biocide created at the beginning of this boundary layer is confined to this layer, is swept along its length, and thus covers the lateral length of hull.

In regards to (5) experiments determined that for a dense algae bloom, 0.4 ppm applied chlorine, as determined by equation (1), eliminated the algae completely with minutes.

In regards to (6) the satellite system now in use to monitor in real time the conductivity and temperature at moorings and floats will be used for two-way communications, in particular with the chlorine generation system. The use of satellite communications with buoys will provide feedback to the in situ chlorine generator. An algae sensor, such as a conductivity cell or a fluorescence detector, is used to determine when algae growth has begun to impair their operation, and then the biocide action is initiated locally or remotely. This latter feature is designed to conserve electrical power, and to focus the antibiofouling where needed.

In regards to (7), integral to the effectiveness of the chlorite plume/film is the shape of the sensor to be protected, both from the biocide coverage and the sensor's tendency to collect algae. It is known that in applications at sea where biofouling was not a problem, after about 3 months the collection of sediments and other debris became a problem. The best shape from both a biofouling and a sediment perspective is a very smooth, glass planar surface, such as a flat window. Probably the only way to achieve multi-year unattended deployment of coastal ocean sensors is with this type surface. A planar window for sensing the index of refraction, called a Critical Wavelength Refractometer (CWR), as well as the algorithm to go with it, allows the efficient coverage of the hydrochlorite plume across a planar surface for most orientations of that surface to gravity.

In regards to (8) the microprocessor will coordinate the operation of the satellite communications, the analysis of the algae sensor data and the activation of the chlorine biocide.

FIG. 1, including FIG. 1(*a*), FIG. 1(*b*), and FIG. 1(*c*), illustrates the basic electrode collar for producing the chlorine biocide in seawater. The cathode 101 is the negative electrode and the anode 102 is the positive electrode, both generally being of platinum or titanium metal. To facilitate attaching electrical wires the platinum can be plated over a thin copper or brass base. When a voltage is applied across these electrodes hydrogen bubbles are produced at 101 and halogen biocide is produced at 102. The cathode is placed above and/or outside of the anode so that the bubbles will be carried away from the sensor area, and the chlorine biocide will be within the moving boundary layer of the sensor. The edges of the electrodes and insulating material are beveled so as not to allow bubbles to collect. The collar is placed close to and above the sensor so that the downward boundary layer plume will move over the sensor area, and the diameter 103 is designed to be equal to the outer diameter of the upper part of the sensor. The hinge 104 allows the installation and removal of the collar, and the latch 105 provides for firmly emplacing the collar on the sensor instrument. The jump wire 106 connects both sides of the electrodes and wires 107 connect each electrode to the electrical DC power source 109 via the microprocessor, computer 108 and communication system (e.g., satellite communication) 110. The power required is generally 2 to 15 volts with current of 10 to 100 milliamperes. In order to remove any scaling that might occur over time, the computer 108 can reverse the polarity of the voltage to electrodes 101 and 102.

Another embodiment of the collar electrode of FIG. 1, shown in FIG. 1(*c*) for use on sensors that draw seawater into an inlet 114, such as with moored instruments, places the anode 112 on the inside of the collar and the cathode 111 on the outside, with the end 113 of the collar extending beyond the inlet 114 to the sensor, so that the biocide is drawn into the sensor by gravity and the hydrogen bubbles rise outside clear of the sensor inlet.

Figure 2:
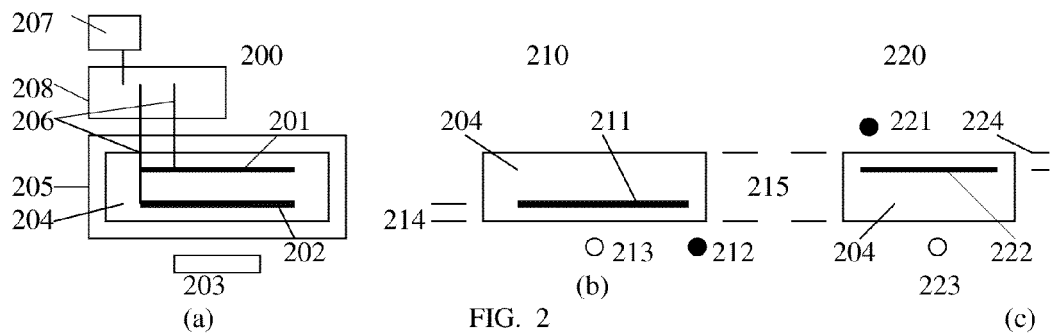
FIG. 2, including

FIG. 2, including FIG. 2(*a*), FIG. 2(*b*), and FIG. 2(*c*), illustrates a second embodiment of the electrode configuration to produce the biocide, as a kit for emplacement in difficult to reach locations and for small, local areas of concern. A thin, flexible platinum anode film 202 is deposited on a thin, flexible dielectric material 204, with adhesive material on its back side 205. The cathode is also deposited on the dielectric material 204 as a thin, flexible platinum or titanium strip 201. The anode 202 is below the cathode 201. The dielectric material 204 is adhered to the instrument body 200 with permanent or removable adhesive 205 and just above the sensor or current meter to be protected from biofouling. The electrical wires 206 are connected to a direct current power supply 207 via computer 208. The computer 208 has the capability of reversing the polarity to cathode 201 and anode 202 if scaling becomes a problem. FIG. 2(*b*) and FIG. 2(*c*) illustrate variations on FIG. 2(*a*) used for smaller sensors with low power requirements, and where the metal instrument body 200 acts as one of the electrodes. In FIG. 2(*b*) and for use on titanium bodied instruments 210, the titanium hull is the anode 212, most effectively just below cathode 211, which is a thin, flexible platinum or titanium strip 211 deposited on a thin, flexible dielectric material 204. The sensor 213 is just below the dielectric material 204. In order that the cathode always be above the anode to eliminate the interference of hydrogen bubbles with the sensor, the cathode 211 is located at the bottom of the dielectric material 204, such that distance 215 is approximately 5 times greater than the distance 214, so that 95% of the current going between the cathode and the anode, and the biocide thusly produced, occurs between cathode 211 and that part of the hull 210 between sensor 213 and the cathode 211. Wires 206, power supply 207 and computer 208 are as in FIG. 2(*a*). In FIG. 2(*c*) and for use on non-titanium metal instrument bodies 220, the hull 220 is the cathode 221, and the anode is a thin, flexible platinum strip 222 deposited at the top of the thin, flexible dielectric material 204. Again, to keep the cathode 221 above the anode 222, the distance 215 is 5 times the distance 224 so that the hydrogen bubbles are produced on the opposite side of the dielectric material 204 and rise upwards from the sensor 223. Wires 206, power supply 207 and computer 208 are as in FIG. 2(*a*).

Figure 3:
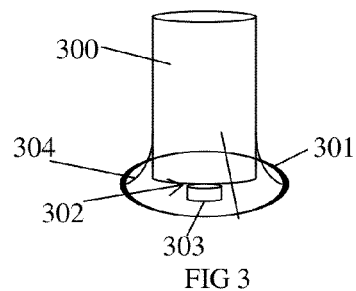
FIG. 3 illustrates a configuration of the antibiofouling electrodes on a generic ocean instrument package.

FIG. 3 illustrates antibiofouling for a generic instrument for use in measuring such parameters as temperature, conductivity, pressure, sound and optical transmissivity in the coastal oceans, and on off-shore oil installations. In general it has a vertical cylindrical body 300 with the sensor package at the bottom end 303 with a circular guard 301 around it. Metal band 302 is the platinum anode (positive terminal) located above the sensor and creating a halogen compound plume heavier than salt water that moves down in the instrument's boundary layer. The guard 301 is the cathode (negative terminal) located outside of the anode 302 and about 50-mm away, thus completing the circuit and creating the generation of free and combined halogen biocide protection for the sensor package. Strut 304 insulates the cathode from the instrument body 300, and contains the wire for the cathode 301.

Figure 4:
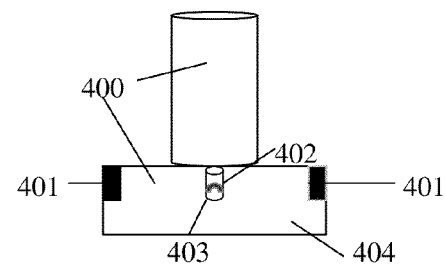
FIG. 4 illustrates an electrode antibiofouling configuration for an inductive cell conductivity sensor.

FIG. 4 illustrates antibiofouling for an inductive cell conductivity sensor 400, commonly used in oceanography. The anode 402 that produces the halogen compound biocide film resides above the conductivity cell 403. The cathode 401 resides outside of, above and is insulated from the enclosure 404. When activated the halogen biocide cylindrical film moves downward around the sensor 403 eliminating algae within a few minutes.

Figure 5:
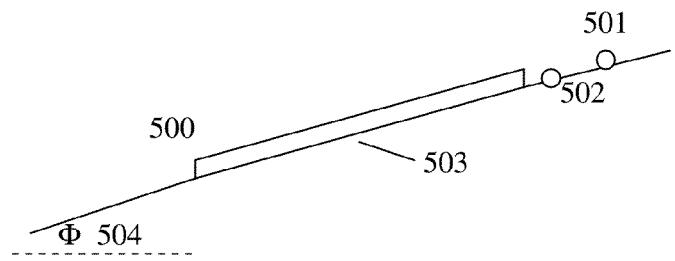
FIG. 5 illustrates an electrode antibiofouling configuration for the glass sensing window of a Critical Wavelength Refractometer.

FIG. 5 illustrates antibiofouling for a flat glass window sensor. Sensor window 503 is orientated at an angle Φ to the horizontal, Φ 504 being generally greater than 5 degrees. Anode 502 is a platinum strip located above the glass window 503 and cathode 501 is a platinum or titanium strip located above the anode so that when a voltage is applied across the electrodes the halogen biocide plume from the anode flows down past the window sensor 503 and the hydrogen bubbles released by cathode 502 rise above window 503. The distance between the anode and the glass window is several widths of the platinum strip in order to prevent any debris from the anode action from reaching the window, and the cathode is placed several strip widths above the anode to prevent any short circuiting of the electrodes by debris.

Figure 6:
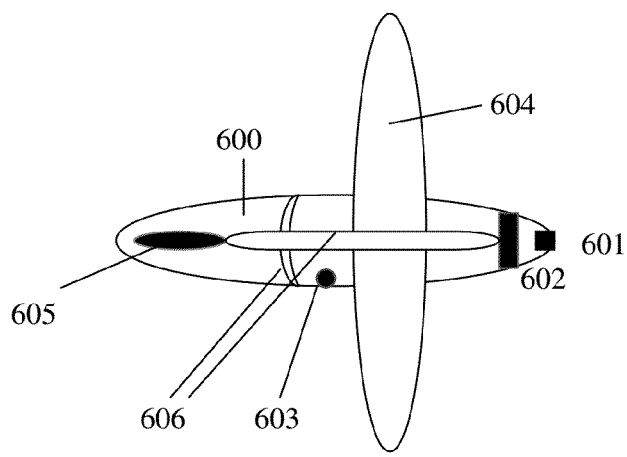
FIG. 6 illustrates an antibiofouling electrode configuration for a submersible robot glider, showing metal seams and fiberglass and/or carbon fiber body.

FIG. 6 illustrates antibiofouling for an ocean glider intended to traverse large tracts of the open ocean unmanned and unattended, but surfacing every few days to communicate by satellite to its home base. As the glider has a limited power supply, its range is dependent upon its speed, which is determined upon how clean its hull remains. Traditionally, after a month the gliders begin to slow and become less maneuverable due to the growth first of algae and then of macrophytes and barnacles. In order to prevent the first stages of this growth, antibiofouling electrodes are placed on the glider. Anode 602, located at the nose of the glider and cathode 601, located just forward of the anode, are activated by a small voltage, of order 3 to 10 volts, by either an on-board algae sensor or by satellite communications when the glider's speed is determined to have been reduced. The halogen biocide is injected into the boundary layer as the glider moves slowly through the water and is carried back along the length of the glider's hull 600. In addition, at certain strategic points on the hull 600, on wings 604 and on rudder 605, such as at metal seams 606 and sensors 603 that are more prone to biofouling, additional anode/cathode pairs are emplaced forward of those locations. Antibiofouling applications similar to those of the above gliders apply also to the NASA ARGOS floats, particularly in their near-surface period of operation.

Figure 7:
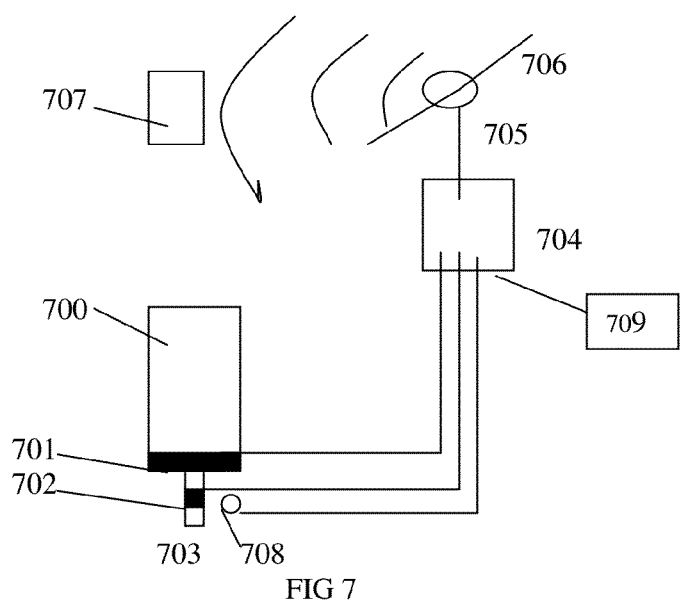
FIG. 7 illustrates a computer and satellite communication and feedback system to activate halogen biocide production when incipient biofouling is detected and FIG. 8 illustrates the electrode configuration for the antibiofouling of the hulls of ships.

FIG. 7 illustrates the communication and decision-making system used to activate the halogen biocide antibiofouling invention. The anode/cathode halogen micro-generator 702/701 is activated by the microprocessor and computer 704 and power supply 709 which receives input from an algae sensor 708, which may be a conductivity or fluorescence sensor, or from other sensors on instrument 700 such as depth and temperature sensors, or via antenna 705 and satellite 706 from command center 707 to prevent algae film developing on environmental sensor 703 as soon as it forms.

Figure 8:
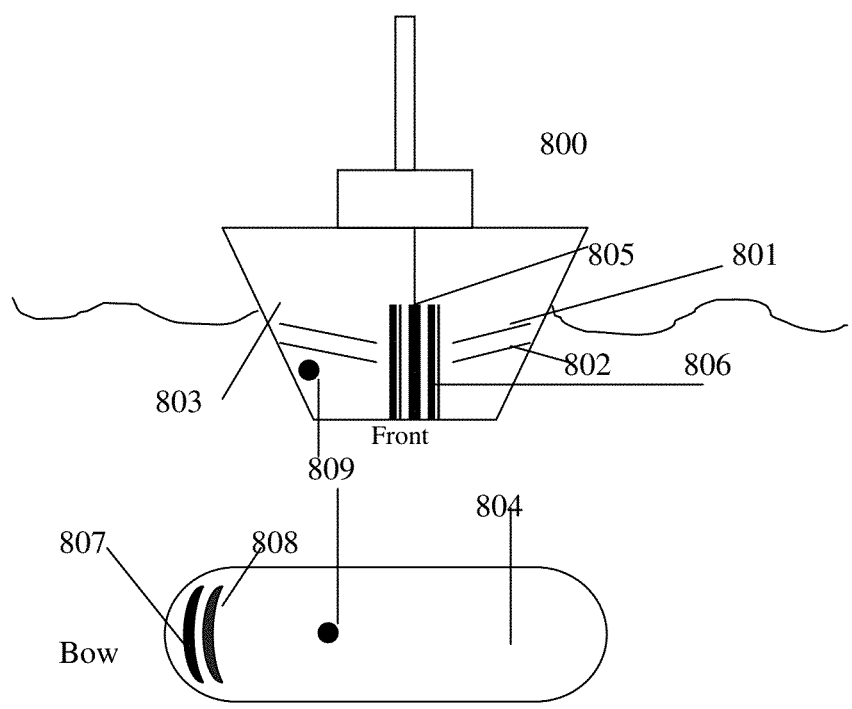

FIG. 8 illustrates an electrode configuration for the halogen biocide generator system employed for the prevention of biofouling on the hull of ships. On the sides of the ship horizontal cathode 801 is placed just below the waterline and horizontal anode 802 is placed just below that, both running the length of the hull 803 of the ship. Also, vertical cathode 805 and anode 806 located at the bow of the ship and beginning just below the waterline provide for greater coverage of the vertical and nearly vertical parts of the hull. The flat or nearly flat bottom of the hull 804 has cathode 807 and anode 808 extending from the tip of the bow to the point where the sides of the ship 800 are parallel. For long hulls a second set of cathode/anode pairs may be placed further back towards the vessel's stern to recharge the biocide in the hull's boundary layer. When the halogen biocide is activated from within the ship, halogen is released into the ship's boundary layer by gravity for cathode/anode 801 and 802, and by the forward motion of the ship for cathode/anode pairs 805/806 and 807/808, the latter being carried horizontally by the ship's motion the length of the hull. The ship's control center interrogates the algae sensors 809 to determine when an algae film is forming and activates some or all of electrodes 801/802, 805/806 and 807/808, said interrogation being accomplished by several means, one in particular being acoustically through the hull 803 and 804.

As noted herein, the system and process are most preferably implemented with a description that includes stating that one electrode is "above" another. This is a preferred implementation for a relatively stationary system that generates a halogen biocide in situ. The particular arrangement, as discussed above, permits any generated gas to be produced from an electrode above the biocide generating electrode, and the biocide, preferably one heavier than water, to "fall" undisturbed by the gas bubbles at the other electrode, and to produce or be constrained by, a boundary layer between the sensor and the water volume. The terms above and below also contemplate, for alternate embodiments, upstream and downstream, where there is relative motion between one or more of the sensor and the surrounding water (such as when mounted to a hull of a water vessel or the sensor is disposed in a water current). Additionally, the embodiments of the present invention apply a voltage potential to a volume of salt water, and this is preferably done through use of two or more electrodes, two electrodes being required to complete the desired electrical circuit. In some cases, embodiments of the present invention employ a portion of a metal wall of a device effectively as one of the "electrodes" thus the electrodes of the present invention may include portions of the walls of devices and is not limited to separate distinct electrodes as it includes "integrated" effective electrodes as well. Frequently chlorine is specifically identified as the halogen of choice in forming the various biocides. It is understood that other halogen biocides are contemplated, as well as other biocides that conform to the identified parameters identified herein, and it is understood that the use of one implies any of the others, unless the context clearly dictates otherwise.

The system and methods above has been described in general terms as an aid to understanding details of preferred embodiments of the present invention. Other preferred embodiments of the present include the described application for strategic retrofit in situ biocide generation. In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A method for effecting an in situ generation of biocide as an aid in anti-biofouling of an external surface of a device disposed in a volume of salt water, the volume greater than a displacement volume of the device, the method comprising the steps of:
   a) associating a cathode electrode to the external surface of the device;
   b) associating an anode electrode to the external surface of the device with said anode electrode spaced apart from said cathode electrode; and
   c) hydrolyzing one or more components in the volume of salt water which generates a halogen biocide at said anode electrode with said halogen biocide flowing from said anode electrode away from said cathode electrode within a biocide layer, said biocide layer responsive to a physical arrangement of said associations of said electrodes with the device;
   wherein at least one of said electrodes includes titanium.

2. A method for effecting an in situ generation of biocide as an aid in anti-biofouling of an external surface of a device disposed in a volume of salt water, the volume greater than a displacement volume of the device, the method comprising the steps of:
   a) associating a cathode electrode to the external surface of the device;
   b) associating an anode electrode to the external surface of the device with said anode electrode spaced apart from said cathode electrode; and
   c) hydrolyzing, responsive to a control signal, one or more components in the volume of salt water which generates a halogen biocide at said anode electrode with said halogen biocide flowing from said anode electrode away from said cathode electrode within a biocide layer, said biocide layer responsive to a physical arrangement of said associations of said electrodes with the device;
   further including a biofouling detection system detecting an initiation of biofouling of a portion of the external surface; and
   d) asserting said control signal responsive to said initiation of biofouling.

3. A method for effecting an in situ generation of biocide as an aid in anti-biofouling of an external surface of a device disposed in a volume of salt water, the volume greater than a displacement volume of the device, the method comprising the steps of:
   a) associating a cathode electrode to the external surface of the device;
   b) associating an anode electrode to the external surface of the device with said anode electrode spaced apart from said cathode electrode; and
   c) hydrolyzing, responsive to a control signal, one or more components in the volume of salt water which generates a halogen biocide at said anode electrode with said halogen biocide flowing from said anode electrode away from said cathode electrode within a biocide layer, said biocide layer responsive to a physical arrangement of said associations of said electrodes with the device;
   further including a biofouling detection system detecting an initiation of biofouling of a portion of the external surface; and
   d) asserting said control signal responsive to said initiation of biofouling wherein said biofouling detection system includes a sensor and a source of blue light selectively illuminating said portion of the external surface with a blue light illumination, said biofouling detection system detecting said initiation of biofouling responsive to a red fluorescence from said initiation of biofouling on said portion.

* * * * *